(12) United States Patent
Ayme-Dietrich et al.

(10) Patent No.: US 11,116,741 B2
(45) Date of Patent: Sep. 14, 2021

(54) METHOD FOR THE TREATMENT OF VALVULAR HEART DISEASE COMPRISING ADMINISTERING A COMPOSITION COMPRISING SARPOGRELATE

(71) Applicant: CEVA SANTE ANIMALE, Libourne (FR)

(72) Inventors: Estelle Ayme-Dietrich, Strasbourg (FR); Jérôme Guyonnet, Ambares (FR); Roland Lawson, Strasbourg (FR); Luc Maroteaux, Paris (FR); Laurent Monassier, Strasbourg (FR)

(73) Assignee: CEVA SANTE ANIMALE, Libourne (FR)

( * ) Notice: Subject to any disclaimer, the term of this patent is extended or adjusted under 35 U.S.C. 154(b) by 56 days.

(21) Appl. No.: 16/604,575

(22) PCT Filed: Apr. 11, 2018

(86) PCT No.: PCT/EP2018/059295
§ 371 (c)(1),
(2) Date: Oct. 11, 2019

(87) PCT Pub. No.: WO2018/189246
PCT Pub. Date: Oct. 18, 2018

(65) Prior Publication Data
US 2020/0297685 A1 Sep. 24, 2020

(30) Foreign Application Priority Data

Apr. 11, 2017 (EP) .................................... 17165863
Jul. 6, 2017 (EP) .................................... 17180011

(51) Int. Cl.
*A61K 31/195* (2006.01)
*C07C 62/10* (2006.01)
*A61K 31/216* (2006.01)
*A61K 9/00* (2006.01)
*A61K 31/4704* (2006.01)
*A61K 31/501* (2006.01)

(52) U.S. Cl.
CPC .......... *A61K 31/216* (2013.01); *A61K 9/0019* (2013.01); *A61K 9/0053* (2013.01); *A61K 31/4704* (2013.01); *A61K 31/501* (2013.01)

(58) Field of Classification Search
CPC .............................. A61K 31/195; C07C 62/10
USPC .......................................... 514/571; 562/507
See application file for complete search history.

(56) References Cited

PUBLICATIONS

Maroteaux, L. et al. "New therapeutic opportunities for 5-HT$_2$ receptor ligands" *Pharmacoloy & Therapeutics*, 2017, pp. 14-36, vol. 170.
Kato, S. et al. "Suppressive Effect of Sarpogrelate Hydrochloride on Respiratory Failure and Right Ventricular Failure with Pulmonary Hypertension in Patients with Systemic Sclerosis" *The Journal of International Medical Research*, 2000, pp. 258-268, vol. 28, No. 6.
Hironaka, E. et al. "Serotonin receptor antagonist inhibits monocrotaline-induced pulmonary hypertension and prolongs survival in rats" *Cardiovascular Research*, 2003, pp. 692-699, vol. 60, No. 3.
Written Opinion in International Application No. PCT/EP2018/059295, dated Jun. 21, 2018, pp. 1-5.

*Primary Examiner* — Douglas M Willis
(74) *Attorney, Agent, or Firm* — Saliwanchik, Lloyd & Eisenschenk

(57) ABSTRACT

The present invention relates to the use of a serotoninergic receptor antagonist, such as sarpogrelate or compositions thereof, for the treatment and/or prevention of heart damages in mammals.

14 Claims, No Drawings

METHOD FOR THE TREATMENT OF VALVULAR HEART DISEASE COMPRISING ADMINISTERING A COMPOSITION COMPRISING SARPOGRELATE

CROSS-REFERENCE TO RELATED APPLICATION

This application is the U.S. national stage application of International Patent Application No. PCT/EP2018/059295, filed Apr. 11, 2018.

FIELD OF THE INVENTION

The invention relates to a pharmaceutical or a veterinary composition comprising sarpogrelate, or a salt thereof, and to the use of said composition for the treatment and/or prevention of heart diseases in mammals, especially in non-human mammals. More particularly, the invention relates to a pharmaceutical or a veterinary composition comprising sarpogrelate, or a salt thereof, for use in the treatment and/or prevention of a valvular heart disease in humans or pets, more especially dogs.

BACKGROUND OF THE INVENTION

Mammals, especially non-human mammals, may suffer from many heart diseases like: vasospastic angina, ischemic heart disease, congenital heart defect, pulmonary hypertension, valvular heart disease.

In dogs, valvular heart disease (VHD), also named myxomatous mitral valve degeneration (MMVD), degenerative mitral valve disease (DMVD), valvular degenerative disease (VDD) or valvulopathy, is a frequent cardiac disease due to the degeneration or lesions of cardiac valves. This degeneration is often linked to valve impermeability which in turn causes blood backflow in the auricle at each heart beat. It leads to a decrease of the blood volume sent to the arteries hence, to a massive increase of the mitral valve thickness.

In humans, VHD is a continuous process developing on a congenital abnormal valve (mitral valve prolapse, bicuspid aortic valve . . . ) or following acquired conditions (cardiovascular risk factors, endocarditis, drug-induced valvulopathy . . . ). VHD becomes increasingly prevalent, due to aging of the population (2.5% between 55 and 64 years, then 4.5% between 65 and 74 years, and more than 10% in people more than 75 years, Nkomo V T et al., 2006). Unfortunately, no therapeutic target has yet been identified to prevent or treat the VHD. Therefore, surgical repair or replacement remain the most effective options, despite the random life expectancy of bioprostheses or the price of anticoagulant treatment risks for life formechanic prostheses.

The functional consequence of VHD is an increase in volume and/or pressure load to the heart muscle leading to heart failure and its consequences, shortness of breath (or dyspnea), cough, renal failure or pulmonary edema. Furthermore, genetics, stress, anxiety, hypoxia, infectious or endocrine disorders can worsen this disease.

In dogs, the degenerative changes of valvulopathy are characterized by an overproduction and deposition of extracellular matrix with disruption of collagen content and organization in the leaflet and chordae tendineae (Serotonin Concentrations in Platelets, Plasma, Mitral Valve Leaflet, and Left Ventricular Myocardial Tissue in Dogs with Myxomatous Mitral Valve Disease, S. E. Cremer et al., J Vet Intern Med 2014; 1-3).

MMVD mainly affects small dogs like Cavalier King Charles, Yorkshire terrier, poodle and the like.

Numerous observations such as drug-induced valvulopathy (induced by ergot (Van Camp et al 2004) and fenfluramine derivatives (Connolly et al 1997), or induced by drugs against Parkinson disease or hyperprolactinaemia, such as apomorphine, pergolide, ropinirole, pramipexole, lisuride, bromocriptine, cabergoline, quinagolide) or carcinoid heart disease (valvulopathy associated with excess of plasma serotonin, secreted by neuroendocrine tumors (Lundin et al 1988) argued in favor of the involvement of the serotonergic system.

In dogs, numerous lines of evidence suggest that 5-HT (and related molecules such as TGF-beta) plays a critical role in the pathogenesis of this disease (Oyama et al.). A variety of investigative techniques, including gene expression, immunohistochemistry, protein blotting, and cell culture, shed light on the potential role of 5HT in the differentiation of valvular interstitial cell (VIC), elaboration of myxomatous extracellular matrix components, and activation of mitogen-activated protein kinase pathways have been used to support the hypothesis that 5-HT and its related pathways serve as an important stimulus in canine valvulopathy (Oyama M A, Levy R J. J Vet Intern Med. 2010. 24 (1). 27-36).

Serotonin (or 5-hydroxytryptamine, 5-HT) is the endogenous ligand of $5\text{-}HT_2$ receptors. It is, a bio-amine mainly localized in the periphery (>95%). Serotonin is synthesized by enterochromaffin cells in the gut, released into the portal circulation and loaded into platelets via the 5-HT transporter (SERT).

Platelet 5-HT content is significantly higher in dogs with valvulopathy compared to healthy non-CKCS (cavalier King Charles) dogs. Moreover, platelet 5-HT content is higher in healthy CKCS compared to healthy dogs of other breeds, supporting potential involvement of platelet-derived 5-HT in the pathogenesis of valvulopathy in this breed. (S. E. Cremer, G. E. Singletary, L. H. Olsen, K. Wallace, J. Häggström, I. Ljungvall, K. Höglund, C. A. Reynolds, N. Pizzinat, and M. A. Oyama. J Vet Intern Med 2014, 1-3).

Peripheral 5-HT and $5\text{-}HT_2$ (5-hydroxytryptamine) receptors contribution to the remodeling of cardiovascular tissues was emphasized recently, particularly in cardiac hypertrophy and valve remodeling (Monassier et al., 2004, 2008; Ayme-Dietrich et al., 2012). $5\text{-}HT_2$ receptors are undetectable or expressed at very low level in normal animals and humans but appear when a stressor is applied. An association between endogenous serotonin, released in the blood stream by platelets, and mitral regurgitation can be noticed (Tse et al., 1997). Moreover, in this last study, the degree of platelet activation was positively correlated with the severity of mitral regurgitation, and independent of the underlying etiology of mitral valve disease, age and left atrial size. Another older study reports an association between mitral valve prolapse and platelet activation leading to the increase of thrombo-embolism in this small cohort (Walsh P N et al., 1981).

More than two decades ago, Brandt et al. discovered that patients with aortic stenosis presented an increase of free serotonin blood levels, attributed to platelet activation (1992). Recently, Rouzaud-Labordeet et al. confirmed that arterial circulating serotonin, serotonin degradation and platelet activation increased in patients with aortic stenosis (2015).

To summarize this data, both valvular lesions, mitral valve prolapse and aortic stenosis (the both most frequent etiology of degenerative heart valve disease (lung B. et al., 2003)) are associated with systemic platelet activation. These observations suggest that the serotonergic system may contribute to the pathogenesis of aortic stenosis and mitral regurgitation, and lead us to hypothesize that an antiplatelet drug could prevent and/or inhibit the serotonin induced valve lesions due to platelet activation.

Unfortunately, there is to date no medical cure for this heart disease in mammals, especially dogs, the only way to treat this disease is surgery. Nevertheless, a few existing medicines allow to improve the wellbeing, through a stabilization of myocardial remodeling and slowing of the heart failing process.

Studies have shown that many drugs (like fenfluramine) and their metabolites (norfenfluramine) are agonists of the 5-$HT_2$ serotoninergic receptors. Moreover, it has been shown that a chronic stimulation of serotoninergic receptors 5-$HT_2$, which can be due to a drug treatment, induces damages of cardiac valves (Blanc—SVSE 1—Physiologie, physiopathologie, santé publique (Blanc SVSE 1) 2012, Projet SEROVALVE).

Two types of 5-$HT_2$ receptors are particularly involved: the 5-$HT_{2A}$ and 5-$HT_{2B}$. It has further been shown that agonists of these receptors have a significant affinity to the specific 5-$HT_{2B}$ receptor subtype (Circulation 2000; 102: 2836-2841, Fitzgerald et al 2000; Rothman et al 2000).

These observations lead to the hypothesis that cardiac valves express a "serotonergic system" that could be activated by 5-HT agonists leading to remodeling and degeneration. Hence, one of the possible solutions to avoid valvular heart diseases consists in decreasing the endogenous serotonin production and/or in using 5-$HT_2$ receptor antagonists, and more particularly, 5-$HT_{2B}$ receptor antagonists.

Kou-Gi Shyu has shown that serotonin, via the 5-$HT_{2B}$ receptor, regulates cardiac development. Serotonin plasma level and serotonin activity are increased in animal studies with cardiac hypertrophy. It may indicate that serotonin induces cardiac hypertrophy or heart failure through the 5-$HT_{2B}$ receptor (Serotonin 5-$HT_{2B}$ Receptor in Cardiac Fibroblast Contributes to Cardiac Hypertrophy A New Therapeutic Target for Heart Failure, Circ Res. 2009; 104: 1-3).

Drug antagonists of the 5-$HT_{2B}$ receptor such as: agomelatine, aripiprazole, SB204741, SB200646, SB228357 and many others are well known. But only a few of them have been confirmed as antagonists of the 5-$HT_{2A}$ receptor. Moreover, it has been highlighted that sarpogrelate is a drug acting as an antagonist to the 5-$HT_{2A}$ and 5-$HT_{2B}$ receptors, with a preference for the 5-$HT_{2A}$ receptor.

Rashid, M; et al. have shown that sarpogrelate is an antagonist preferably blocking the 5-$HT_{2A}$ receptor compared to the 5-$HT_{2B}$ one (2003b. Identification of the binding sites and selectivity of sarpogrelate, a novel 5-$HT_2$ antagonist, to human 5-$HT_{2A}$, 5-HT2B and 5-$HT_{2C}$ receptor subtypes by molecular modeling. Life Sci. 73, 193-207).

Sarpogrelate has been used to treat several heart diseases, but has never been associated with prevention nor treatment of valvular heart damages.

Tatsuya Muto et al. have shown that the sarpogrelate is a good antagonist against postischemic myocardial dysfunction in guinea-pig hearts (Molecular and Cellular Biochemistry April 2005, Volume 272, Issue 1, pp 119-132).

Miho Sekiguchi et al. investigated the effects of a 5-$HT_{2A}$ receptor antagonist on blood flow in lumbar disc herniation applied in a canine model (European Spine Journal February 2008, Volume 17, Issue 2, pp 307-313).

Sarpogrelate or other 5-$HT_{2A}$ antagonists may have clinical potential for the treatment of vasospastic angina, ischemic heart disease, reperfusion injury and hind-limb ischemia (Expert Opin Investig Drugs. 2003 May; 12(5):805-23; The role of 5-HT on the cardiovascular and renal systems and the clinical potential of 5-HT modulation, Doggrell SA1).

In another study, sarpogrelate was tested for the prevention of the development or progression of diabetic nephropathy (Takahashi, T., et al., Diabetes Res Clin Pract. November 2002; 58(2):123-9).

Sarpogrelate (in combination with ketanserin) has been shown to significantly lower intra ocular pressure in glaucoma patients (Takenaka et al., Investig Ophthalmol Vis Sci 36:S734 (1995).

Many antagonists to the 5-$HT_{2B}$ receptor have been tested to treat heart diseases. However, the idea to specifically target the 5-$HT_{2A}$ receptor hasn't been investigated yet to treat and/or prevent valvular heart damages. The present inventors have surprisingly demonstrated that sarpogrelate is very efficient in decreasing the thickness of the mitral valve, and hence, to treat and/or prevent mitral valvulopathies in mammals (including humans), especially non-human mammals.

SUMMARY OF THE INVENTION

In view of the above, the present inventors surprisingly found that sarpogrelate, or a salt thereof, acting as an antagonist of the 5-$HT_{2A}$ receptor, is efficient to treat and/or prevent the myxomatous mitral valve degeneration (MMVD) in mammals, especially in non-human mammals, more especially dogs.

Therefore, the problem solved by the present invention is to provide a method for the prevention and/or treatment of valvular heart disease induced by a stimulation of the serotoninergic 5-$HT_{2A}$ receptor in non-human mammals and in humans by decreasing the valvular mitral thickness using sarpogrelate, or a salt thereof.

The advantages of sarpogrelate are numerous: it is safe, well accepted by the non human or human body (biocompatible), well absorbed, well distributed, well metabolized, well eliminated, and is finally easy to use as a pharmaceutical or veterinary medicament.

A first object of the invention relates to a pharmaceutical or veterinary composition comprising sarpogrelate, or a salt thereof, for use in the treatment and/or prevention of heart diseases in mammals, especially in non-human mammals, more particularly for the prevention and/or treatment of pulmonary hypertension which induces MMVD, more particularly for the prevention and/or treatment of valvular heart disease, more preferably valvulopathy characterized by an increase of the mitral thickness.

A further object of the invention is a method of treatment and/or prevention of heart diseases in mammals, especially in non-human mammals, comprising administering to said mammals a pharmaceutical or veterinary composition comprising sarpogrelate, or a salt thereof, alone or in association with another active ingredient.

DETAILED DESCRIPTION OF THE INVENTION

In a first aspect, this invention relates, to a pharmaceutical or veterinary composition comprising sarpogrelate, or a salt thereof, for use in the treatment and/or prevention of heart diseases in mammals, especially in non-human mammals.

The pharmaceutical or veterinary composition according to the present invention is preferably used for the prevention and/or treatment of valvular heart disease, and/or for the prevention and/or treatment of pulmonary hypertension associated with VHD, in mammals. The invention relates to a pharmaceutical or a veterinary composition comprising sarpogrelate, or a salt thereof, for use in the treatment and/or prevention of a valvular heart disease in humans or pets, more especially dogs.

The pharmaceutical or veterinary composition is preferably used to decrease the mitral valve thickness in the case where the valvular heart disease is characterized by an increased valvular mitral thickness, and an increased cellularity.

The pharmaceutical or veterinary composition according to the present invention is used in the treatment and/or prevention of valvular heart disease in mammals, wherein the valvular heart disease results from a carcinoid heart disease, wherein the valvular heart disease is associated with a pulmonary hypertension, or wherein the valvular heart disease results from an initial cardiac valve abnormality, or cardiac valve lesions. The composition is also used in pathological situations where VHD is highly prevalent such as hemodialysis for chronic kidney disease.

Within the context of invention "pharmaceutical composition" refers to a composition containing drugs used to treat and/or diagnose and/or cure and/or prevent diseases. Furthermore, a drug is any substance or combination of substances (composition) presented as having properties for treating or preventing disease in human beings; or any substance or combination of substances which may be used in, or administered to human beings either with a view to restoring, correcting or modifying physiological functions by exerting a pharmacological, immunological or metabolic action, or to making a medical diagnosis (according to the Directive 2004/27/EC).

According to the FDA glossary, within the context of invention "pharmaceutical composition" also refers to a "drug product" which is the finished dosage form that contains a drug substance, generally, but not necessarily in association with other active or inactive ingredients.

A drug is defined as a substance recognized by an official pharmacopoeia or formulary, a substance intended for use in the diagnosis, cure, mitigation, treatment, or prevention of disease, a substance (other than food) intended to affect the structure or any function of the body, a substance intended for use as a component of a medicine but not a device or a component, part or accessory of a device (biological products are included within this definition and are generally covered by the same laws and regulations, but differences exist regarding their manufacturing processes—chemical process versus biological process—).

According to the present invention the term "veterinary" has the same definition as "pharmaceutical", but adapted to animals (meaning non human beings): "animal" means any living stage of any member of the animal kingdom except human beings.

More precisely, a "veterinary drug" (or medicine or composition) means any substance or mixture of substances which is used, or is manufactured, sold or represented as suitable for use, in the diagnosis, treatment, control, eradication, mitigation or prevention of disease or abnormal physical or mental state or the symptoms thereof in an animal; or restoring, correcting, controlling, or modifying any physical, mental or organic function in an animal.

Within the context of this invention, sarpogrelate is the (4-[1-dimethylamino-3-[2-[2-(3-methoxyphenyl)ethyl]phenoxy]propan-2-yl]oxy-4-oxobutanoic acid (CAS number 125926-17-2, molar weight 429.5) and has the following chemical structure:

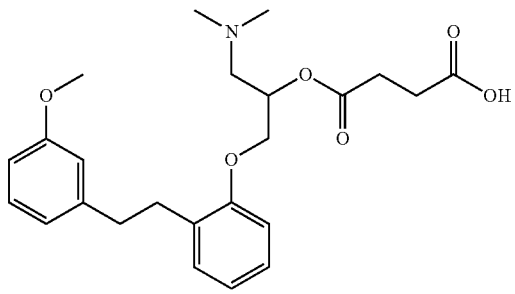 [SMILES: COc1cccc(CCc2ccccc2OCC(CN(C)C)OC(=O)CCC(=O)O)c1]

Within the context of this invention, the term sarpogrelate also comprises its pharmaceutically acceptable salts. These pharmaceutically acceptable salts include inorganic acid salts as well as organic acid salts. The inorganic acid salt can be hydrochloride, hydrobromide, phosphate, nitrate sulfate, and the like. The organic acid salts include fumarate, citrate, tartrate, acetate, maleate, toluenesulfonate, methanesulfonate and the like. Preferably, sarpogrelate is in the form of its hydrochloride salt.

Sarpogrelate hydrochloride has the following formula (CAS number 135159-51-2, molar weight 465.97):

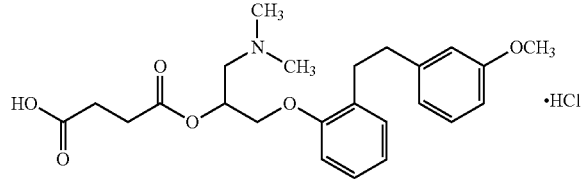 [SMILES: COc1cccc(CCc2ccccc2OCC(CN(C)C)OC(=O)CCC(=O)O)c1 ; Cl]

"Prevent and/or treat" as used herein include the control, the reduction, the progression slowing, the eradication, the cure and/or avoid heart diseases.

Within the context of the invention, heart diseases which can be prevented and/or treated include both induced and spontaneously degenerative valvular cardiac damages such as: MMVD (whatever is origin (congenital or acquired), especially when platelet activation and/or serotonin release lead to valvular lesions), drug-induced valvulopathy, pulmonary hypertension associated with VHD, carcinoid heart disease, pulmonary and/or retroperitoneal and/or valvular fibrosis induced by ergotamine, fibrosis, cardiomyopathy, hypertrophic cardiomyopathy, dilated cardiomyopathy, arrhythmogenic right ventricular myopathy, congenital heart defect, heart failure, congestive heart failure, aortic stenosis, aortic regurgitation, bicuspid aortic valve, mitral valve prolapse, Barlow's disease, rheumatic heart disease, cardiac valve lesions induced by erythropoietin treatment and/or hemodialysis in hemodialysed patients and/or patients with chronic kidney disease, valvular lesions due to the mobilization of endothelial progenitors cells (pathological mechanisms and/or therapeutic treatments), and the like.

Sarpogrelate, or a salt thereof, can also be used for the cardiac protection (valve) of patients placed on mechanical assistance of cardiac pumping function.

Within the context of the invention, pulmonary hypertension can be defined as an increase of blood pressure in the pulmonary artery- vein- or capillaries, known as the lung vasculature, leading to shortness of breath, leg swelling, dizziness, fainting, and other symptoms.

Sarpogrelate reduces cardiac valve thickness, blood mobilization of endothelial progenitors, valvular recruitment of progenitor cells, differentiation of progenitor cells into myofibroblasts, interstitial migration of valvular progenitor cells and finally, cardiac valve remodeling.

Functionally, sarpogrelate reduces heart-valve leaks and stenoses. Moreover, sarpogrelate preserves left ventricular function, reduces cardiovascular morbidity and mortality induced by heart valve disease, and avoid atrial fibrillation, pulmonary hypertension and anticoagulant therapy linked to valvulopathy. Finally, sarpogrelate reduces the degeneration of bioprostheses and delays the onset of cardiac valve replacement.

In a second particular embodiment of this invention, the composition is administered to the animal, more especially to the non human mammal, in a therapeutic dose comprised between 0.5 and 50 mg/kg/day, preferably between 0.5 and 45 mg/kg/day, or 0.5 and 40 mg/kg/day, or 0.5 and 35 mg/kg/day, or 0.5 and 30 mg/kg/day, or 0.5 and 25 mg/kg/day, or 0.5 and 20 mg/kg/day, or 0.5 and 15 mg/kg/day, or 0.5 and 10 mg/kg/day, or 0.5 and 5 mg/kg/day, or 0.5 and 2 mg/kg/day, and more preferably about 2 mg/kg/day.

In a further particular embodiment of this invention, the composition is administered to the animal, more especially to the human mammal, in a therapeutic dose comprised between 10 and 200 mg/kg/day, preferably between 15 and 190 mg/kg/day, or 20 and 180 mg/kg/day, or 25 and 170 mg/kg/day, or 25 and 160 mg/kg/day, or 25 and 140 mg/kg/day, or 30 and 130 mg/kg/day, or 30 and 120 mg/kg/day, or 30 and 110 mg/kg/day, or 30 and 105 mg/kg/day, or 30 and 100 mg/kg/day, and more preferably about 100 mg/kg/day.

In a particular embodiment of this invention, sarpogrelate is administered in a therapeutic dose comprised between 0.5 and 200 mg/kg/day.

In non human mammals, sarpogrelate is administered daily, twice daily, and especially, once daily (extended release). The composition can be administered by oral or parenteral (intradermic, subcutaneous, intravenous, intramuscular, perfusion . . . ) routes.

Furthermore, in human mammals, sarpogrelate is administered between once daily and three times daily, especially between two and three times daily, more especially twice daily, and even more especially three times daily. The composition can be administered by oral or parenteral (intradermic, subcutaneous, intravenous, intramuscular, perfusion . . . ) routes, more especially by oral route. Preferably, the sarpogrelate is administered after meals.

The treated mammals are mammals, meaning humans or non human mammals. In a preferred embodiment, the mammal is a human or a pet.

The treated non-human mammals is preferably a pet, including cats and dog, more preferably a dog. The dog can be a small size dog, a medium size dog or a large size dog. More specifically, the composition is in the form of a liquid solution, suspension, solid or semi-solid, powder, pellet, capsule, granule, sugar-coated pill, gelule, capsule, spray, pill, tablet, paste, implant or gel. The composition is administered by oral or parenteral routes.

The preferred administration for non-human mammals, especially dogs, is an injectable form. The preferred administration for human mammals is an oral form.

The composition for use according to the present invention may further comprise pharmaceutically acceptable additives corresponding to ingredients conventionally used in pharmacy for the preparation of suspensions, liquid or solid formulations for oral or parenteral administrations.

More precisely, the composition for use according to the present invention further comprises buffer agents and/or excipients and/or preservatives and/or oxidants and/or diluents, and/or solubillization agents, and/or lubricants, and/or a solvent, and the like.

For a formulation in tablet or pellet, for an oral administration, monohydrate lactose, magnesium stearate, microcrystalline cellulose, polyvinylpyrrolidone, crospovidone, aromas and compressible sugars can be used as excipients, in a solvent. Examples of solvents for oral route are: propylene glycol, ethanol, sorbitol syrup, water, vegetable oils, or combinations thereof, and the like.

For an injectable formulation, the pharmaceutical composition according to the present invention can be prepared by adding a therapeutically efficient quantity of sarpogrelate, or a salt thereof, in a solvent, with a buffer agent, a suspension agent, a solubilisation agent, a stabilizer, a tonicity agent and/or a preservative.

Examples of solvents include dimethylsulfoxide (DMSO), N-methyl-2-pyrrolidone (NMP), ethanol, diester propylene glycol, propylene glycol, or combinations thereof, and the like.

Examples of buffer agents are calcium phosphate, sodium bicarbonate, sodium phosphate, sodium lactate, sodium citrate, or combinations thereof, and the like.

Examples of suspension agents include methylcellulose, hydroxypropylmethylcellulose, polysorbate 80, hydroxyethylcellulose, hydroxycellulose, anthan gum, sodic carboxymethylcellulose and polyethoxylated sorbitan monolaurate, or combinations thereof, and the like.

Moreover, the stabilizer includes sodium sulfite, sodium metalsulfite and ether, while the preservative includes methyl p-hydroxybenzoate, ethyl p-hydroxybenzoate, sorbic acid, phenol, cresol, chlorocresol, polyvinylpirrolidone, sorbitol syrup . . . or combinations thereof, and the like.

Examples of tonicity agent are mannitol, sodium chloride, sodium citrate glycerin, lactose, mannitol, sodium chloride, dextrose, sodium sulfate, sorbitol, or combinations thereof, and the like.

Examples of preservatives are ethyl p-hydroxybenzoate, w-propyl p-hydroxybenzoate, methyl p-hydroxybenzoate, sorbic acid, phenol, cresol, chlorocresol, benzoic acid or salts thereof, sodium metabisulfite, sodium benzoate, benzethonium chloride, cetylpyridinium chloride, benzalkonium chloride, sodium acetate, parabenes and salts thereof, sucrose, or combinations thereof, or combinations thereof, and the like.

The composition may further comprise other excipients like solubilization agents, antioxidants, diluents, aromas (apricot, vanilla, beef), lubricants, surfactants, wetting agent.

Examples of solubilization agents include polyoxyethylene-solidified castor oil, polysorbate 80, nicotinamide, polyethoxylated sorbitan monolaurate, macrogol and ethyl ester of caste oil fatty acid, or combinations thereof, or combinations thereof, and the like.

Examples of diluents are calcium carbonate, calcium phosphate, kaolin, sodium carbonate, lactose, sodium phosphate, lactose monohydrate, or combinations thereof, and the like.

Examples of antioxidants include: ascorbic acid (vitamin C) or salts thereof, citric acid or salts thereof, malic acid, monothioglycerol, fumaric acid, phosphoric acid, sodium metabisulfite, potassium metabisulfite, propionic acid, sodium bisulfitesodium metabisulfite, potassium metabisulfite, vitamin E (tocopherol), acetone, cystein, gentisic acid ethanolamine, glutamate monosodium, formaldehyde sulfoxylate sodium, or combinations thereof, and the like.

Lubricants may be selected from: oils, waxes, stearic acid, stearates (magnesium stearate, calcium stearate), talc, long chain fatty acids, polyethylene glycol, palmitic acid, hydrogenated vegetable oils, sodium stearyl fumarate, sodium benzoate, and mixtures thereof.

Surfactants may be selected from poloxamer, polysorbate, polyoxyethylene hydrogenated castor oil . . . ) and mixtures thereof.

Wetting agent may be ethanol, and the like.

The concentration of sarpogrelate or a salt thereof in the composition according to the invention depends on the route of administration, the symptoms, the age of the animal (meaning mammals, non humans and humans). For a non human mammal, in the form of an injectable solution, the composition may comprise between 0.5 and 130 mg/mL of sarpogrelate, or a salt thereof. A solid composition may comprise between 10 and 80 mg of sarpogrelate, or a salt thereof.

For a human mammal, a solid (oral) composition may comprise between 10 and 200 mg of sarpogrelate, or a salt thereof.

The pharmaceutical or veterinary composition for use according to the present invention may further comprise another active ingredient, more specifically one or more active ingredients, conventionally used to treat cardiac diseases. Preferably, the other active ingredient, more specifically the one or more active ingredients, is (are) selected from: a phosphodiesterase inhibitor, and/or an arterial vasodilator, and/or a diuretic, and/or an angiotensin-converting-enzyme inhibitor (ACE inhibitor), and/or an angiotensin II receptor antagonist, and/or or a platelet aggregation inhibitor, and/or an anorexigen, and/or an anti-migraine drug.

More particularly, the preferred phosphodiesterase inhibitor is selected from cilostazol, pimobendan, caffeine, aminophylline, 3-isobutyl-1-methylxanthine, paraxanthine, pentoxyfilline, theobromine, theophylline, vinpocetine, oxindole, mesembrenone, rolipram, ibudilast, luteolin, drotaverine, piclamilast, roflumilast, apremilast, crisaborole, sildenafil, vardenafil, tadalafil, avanafil, udenafil, dipyridamole, icariin, quinazoline, papaverine, and the like. More particularly, the preferred phosphodiesterase inhibitor is selected from pimobendan, or cilostazol, also named 6-[4-(1-cyclohexyl-1H-tetrazol-5-yl)-butoxy]-3,4-dihydro-2 (1H)-quinolinone (CAS number: 73963-72-1, molar weight: 369.46 g/mol):

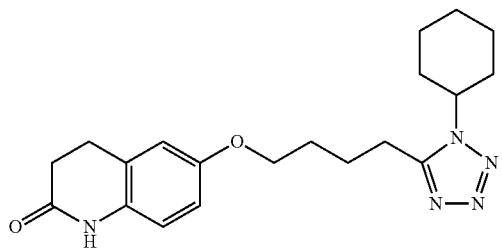 [SMILES: O=C1CCc2cc(OCCCCc3nnnn3C3CCCCC3)ccc2N1]

Pimobendan is the preferred phosphodiesterase inhibitor, especially for non human mammals, especially for dogs.

More particularly, the arterial vasodilator is selected from adenosine, adrenaline, bradykinine, histamine, nicotinic acid, nitric oxid, diltiazem, verapamil, nifedipine, captopril, enalapril, hydralazine, prazosine, (acetyl-glyceryl-ether-phosphorylcholine (platelet-activating factor), prostacyclin, isosorbide dinitrate, and the like.

More particularly, the diuretic is selected from amphotericin B, lithium citrate, tolvaptan, conivaptan, dopamine, dorzolamide, acetazolamide, bumetanide, ethacrynic acid, furosemide, torsemide, glucose, mannitol, eplerenone, spironolactone, amiloride, caffeine, theophylline, theobromine, bendroflumethiazide, hydrochlorothiazide, canrenoate, and the like.

More particularly, the ACE inhibitor is selected from captopril, cilazapril, trandolapril, imidapril, benazepril, lisinopril, perindopril, quinapril, ramipril, enalapril, zofenopril, and the like.

More particularly, the preferred angiotensin II receptor antagonist is selected from fimasartan, azilsartan, olmesartan, eprosartan, telmisartan, valsartan, irbesartan, candesartan, losartan, and the like.

More particularly, the platelet aggregation inhibitor is selected from cilostazol, aspirin, clopidogrel, triflusal, prasugrek, ticagrelor, toclopidine, tirofiban, aptifibatide, abciximab, vorapaxar, terutroban, dipyridamole, ADP receptor antagonists, GpIIb/IIIa receptor antagonists, and the like, the preferred one being cilostazol.

More particularly, the anorexigen is selected from dexfenfluramine, diehtylpropion, oxymethazoline, phentermine, benfluorex, butenolide, cathine, phenmetrazine, phenylpropanolamine, and the like, the preferred one being dexfenfluramine.

More particularly, the anti-migraine drug is selected from ergot type medication, like dihydroergotamine, methysergide, ergotamide, ergotamine tartrate, and the like.

More particularly, the active ingredient is cilostazol or pimobendane.

In another embodiment, the present invention also relates to a method of treatment and/or prevention of valvular heart disease and/or pulmonary hypertension in mammals, especially non-human mammals comprising administering to said mammals, especially non-human mammals, a pharmaceutical or veterinary composition comprising sarpogrelate, or a salt thereof. All of the embodiments described above also apply to the present method of treatment.

More particularly, the present invention relates to a method of treatment and/or prevention of valvular heart disease in mammals comprising administering to said mammals a pharmaceutical or veterinary composition comprising sarpogrelate, or a salt thereof.

The following examples below are illustrative and in no way limiting the scope of the present invention.

EXAMPLES

Example 1: Effect of Sarpogrelate in a Mouse Model

In this example, mitral valve leaflet injuries are induced to mice by chronic administration of nordexfenfluramine (NdF), a 5-HT$_{2B}$ agonist. These lesions appear as endothelial cells recruitment and migration into the valvular leaflets with intense production of extracellular matrix.

30 male mice, aged over 12 weeks old, with body a weight around 30 g, were randomly assigned into 3 groups as shown in Table 1.

TABLE 1

Animal groups used in the experiment:

| Treated groups | number of animals (males) |
| --- | --- |
| Control | 10 |
| NdF | 10 |
| NdF + sarpogrelate | 10 |

Before the start of the experiment, baseline systolic blood pressure, heart rate and body weight were measured. After this step, mice were subcutaneously implanted a mini-osmotic pump (Alzet® 1004) delivering either NdF dissolved in sterile water at 1 mg/kg/day or sterile water (vehicle) for 28 days. The dose of sarpogrelate administered was 2 mg/kg/day. The experiment started two days after the subcutaneous implantation so as to allow the activation of the mini-osmotic pump. Systolic blood pressure, heart rate and body weight were measured each week until the end of the experiment. At the term (day 28), urinary samples were collected from mice to determine 5-hydroxy-indol acetic acid concentration (5-HIAA which is a serotonin metabolite). NdF induces the release of serotonin, therefore increasing urinary 5-HIAA.

Then, mice were euthanized using an injection of a non-lethal dose of pentobarbital followed by an intra-cardiac blood puncture and whole blood serotonin concentration was determined.

Blood 5-HT and urine 5-HIAA concentrations were measured during the weeks following the sacrifice, and are summarized in Table 2. All plasma was collected and analyzed in a single run.

TABLE 2

Concentration of 5-HT and 5-HIAA as measured.

| | Control | NdF (mean) | NdF + Sarpogrelate (mean) |
| --- | --- | --- | --- |
| 5-HT (µg/l) | 1915.89 | 2259.78 | 1559.0 |
| 5-HIAA (mg/l) | 27.84 | 10.62 | 7.48 |
| Ratio 5-HT/5-HIAA (µg/l) | 0.0213 | 0.2646 | 0.2278 |

This data clearly shows that the Ndf increases the total blood concentration of serotonin, and conversely sarpogrelate reduces this concentration. As the quantity of 5-HIAA in urine decreases simultaneously, it means a reduction of the 5-HT synthesis.

Measures of body weight (Table 3), food intake (Table 4), water intake (Table 5), systolic blood pressure (Table 6), heart rate (Table 7), effect of sarpogrelate on the cellularity (tables 8-9) and effect of sarpogrelate on reduction of mitral valve thickness (table 10) are shown below.

TABLE 3

Body weight (g)

| | Control | NdF | NdF + Sarpogrelate |
| --- | --- | --- | --- |
| Week 0 | 24.89 | 25.10 | 22.82 |
| Week 1 | 26.11 | 26.20 | 24.36 |
| Week 2 | 26.56 | 26.7 | 24.73 |
| Week 3 | 27.22 | 27.20 | 26.67 |
| Week 4 | 26.00 | 26.50 | 25.44 |

None of the treatments altered the body weight when compared to the control group.

TABLE 4

Food intake: Estimation of the food intake for each mouse per week (g)

| | Control | NdF | NdF + Sarpogrelate |
| --- | --- | --- | --- |
| Week 1 | 30.84 | 32.83 | 34.67 |
| Week 2 | 32.62 | 30.71 | 39.64 |
| Week 3 | 30.28 | 35.13 | 32.24 |
| Week 4 | 25.87 | 26.38 | 35.67 |

None of the treatments altered the food intake when compared to the control group.

TABLE 5

Water intake: Estimation of the water intake per cage per day (g = ml)

| | Control | NdF | NdF + Sarpogrelate |
| --- | --- | --- | --- |
| Week1 | 25.29 | 31.43 | 33.21 |
| Week 2 | 31.29 | 31.86 | 32.86 |
| Week 3 | 30.14 | 32.14 | 30.36 |
| Week 4 | 23.43 | 33.07 | 27.43 |

None of the treatments altered the water intake when compared to the control group.

TABLE 6

Systolic blood pressure (mmHg)

| | Control | NdF | NdF + Sarpogrelate |
| --- | --- | --- | --- |
| Week 0 | 112.8 | 100.2 | 118.8 |
| Week 1 | 105.4 | 108.9 | 105.8 |
| Week 2 | 99.4 | 97.5 | 97.8 |
| Week 3 | 106.7 | 105.6 | 107.2 |
| Week 4 | 106.4 | 99.5 | 109.7 |

None of the treatments altered the blood pressure when compared to the control group.

TABLE 7

Heart rate (beats/min):

| | Control | NdF | NdF + Sarpogrelate |
| --- | --- | --- | --- |
| Week 0 | 563.1 | 539.7 | 513.8 |
| Week 1 | 553.6 | 579.5 | 542.2 |
| Week 2 | 492.7 | 571.8 | 507.0 |
| Week 3 | 579.7 | 498.0 | 514.1 |
| Week 4 | 571.1 | 559.3 | 549.8 |

None of the treatments altered the heart rate when compared to the control group.

For morphometric analysis, one sagittal section (5 µm in thickness) is obtained after paraffin embedding and stained with hematoxylin and eosin stain. In each section, mitral valves are examined and cellularization counted. Extreme care is taken in sectioning the heart so that the valves are mainly cut transversely (with the attachment sides of the leaflets visible on both ends of the valve).

Valve histological morphometric analysis is performed visually using a microscope (Leica DM750®, Germany) with a 40× calibrated objective connected to a camera and a data acquisition and analysis system (Leica/Microsystems®LAS V4.8) by a single operator. Practically, on each section, the operator applies a large square of 250 µm×250 µm divided in 100 equal parts of 25 µm×25 µm each. For the quantification, the whole mitral valve leaflet section is divided in three equal parts. The proximal region is the one nearest the base cusp, followed by the medial and the distal regions. The proximal, medial and distal parts thicknesses are measured on three distinct sites in each region. The mean result is expressed in µm, in table 8.

TABLE 8

Effect of sarpogrelate on reduction of mitral valve thickness

|      | Control | NdF    | NdF + Sarpogrelate |
|------|---------|--------|--------------------|
| Mean | 34.676  | 67.467 | 44.569             |

A massive increase of the mitral valve thickness is induced by NdF. This increased thickness is nearly completely prevented by sarpogrelate.

Tables 9-10: Effect of Sarpogrelate on the Cellularity

The density of endothelial cells is evaluated in proximal, medial and distal regions. The numbers of cells is determined on a leaflet length of 25×4 µm (100 µm2). The result (mean) is expressed in number of cells per 100 µm2.

TABLE 9

Endothelial cellularity (cells/0.01 mm$^2$)

|      | Control | NdF   | NdF + Sarpogrelate |
|------|---------|-------|--------------------|
| Mean | 8.991   | 9.988 | 10.185             |

No significant change of the endothelial cellularity is observed.

TABLE 10

Interstitial cellularity (cells/0.01 mm$^2$)

|      | Control | NdF    | NdF + Sarpogrelate |
|------|---------|--------|--------------------|
| Mean | 14.104  | 22.011 | 16.737             |

An increase in the valve interstitial cellularity is observed with NdF. Sarpogrelate prevents the increase.

To summarize, sarpogrelate reduces plasma 5-HT and urinary 5-HIAA (5-hydroxyindoleacetic acid). This result indicates that sarpogrelate limits 5-HT synthesis and/or platelet release. Moreover, sarpogrelate markedly reduces mitral valve thickness in the above model of NdF induced mitral remodeling attesting the anti-remodeling effect of this 5-HT$_{2A}$ receptor antagonist. Finally, sarpogrelate reduces interstitial migration of endothelial cells, indicating that this receptor is involved in a mechanism linking recruitment and migration of circulating endothelial progenitors.

Example 2: Oral Formulation (1 mg/mL)

1 L of oral solution is prepared by solubilization of 1 g of sarpogrelate hydrochloride and 1 g of benzylic alcohol in distilled water. It is stored in a multiple use glass vial and is physicochemically stable for at least 3 months, at a temperature comprises between 4 and 40° C. The dose is 1 mL for 10 kg of body weight.

Example 3: Oral Formulation (1 mg/mL)

| sarpogrelate hydrochloride   | 1 g    |
| methyl parahydroxybenzoate   | 1.5 mg |
| propyl parahydroxybenzoate   | 0.2 g  |
| hydroxycellulose             | 0.1 g  |
| sucrose                      | 5 g    |
| aroma                        | 0.5 g  |
| distilled water              | Qs 1 L |

1 L of an oral formulation is prepared according to the following process: 1 g of sarpogrelate hydrochloride, 1.5 mg of methyl parahydroxybenzoate, 0.2 g of propyl parahydroxybenzoate, 0.1 g of hydroxycellulose, 5 g of sucrose and 0.5 g of apricot aroma are solubilized in distilled water. It is stored in a multiple use glass vials and is physicochemically stable for at least 3 months, at a temperature comprises between 4 and 40° C. The dose is 1 mL for 10 kg of body weight.

Example 4: Oral Suspension (100 mg/g)

| sarpogrelate hydrochloride       | 100 g  |
| methyl parahydroxybenzoate       | 1.2 mg |
| propyl parahydroxybenzoate       | 0.2 g  |
| hydroxypropylmethylcellulose     | 1 g    |
| ethanol                          | 40 g   |
| sorbitol syrup                   | 60 g   |
| distilled water                  | Qs 1 L |

1 L of an oral suspension is prepared by dispersion of 100 g of micronized sarpogrelate hydrochloride, in 900 g of an aqueous solution comprising 1 g of hypromellose (hydroxypropylmethylcellulose), 40 g of ethanol, 60 g of sorbitol syrup at 70%, 1.2 mg of methyl parahydroxybenzoate and 0.2 g of propyl parahydroxybenzoate. It is stored in a multiple use glass vial and is physicochemically stable for at least 3 months, at a temperature comprises between 4 and 40° C.

Example 5: Oral Suspension (100 mg/g)

| sarpogrelate hydrochloride       | 100 g  |
| methyl parahydroxybenzoate       | 1.5 mg |
| propyl parahydroxybenzoate       | 0.2 g  |
| hydroxypropylmethylcellulose     | 1 g    |
| aroma                            | 0.5 g  |
| sorbitol syrup                   | 100 g  |
| distilled water                  | Qs 1 L |

1 L of an oral suspension is prepared by dispersion of 100 g of micronized sarpogrelate hydrochloride, in 900 g of an aqueous solution comprising 1 g of hypromellose (hydroxypropylmethylcellulose), 100 g of sorbitol syrup, 60 g of sorbitol syrup at 70%, 1.5 mg of methyl parahydroxybenzoate, 0.2 g of propyl parahydroxybenzoate and 0.5 g of vanilla aroma. It is stored in a multiple use glass vial and is physicochemically stable for at least 3 months, at a temperature comprises between 4 and 40° C.

Example 6: Compound: Tablet (50 mg of Sarpogrelate Hydrochloride)

Compounds comprising sarpogrelate hydrochloride are prepared according to a two-steps process:

Step 1: Granulation

| | |
|---|---|
| sarpogrelate hydrochloride | 500 g |
| lactose monohydrate | 250 g |
| microcristalline cellulose | 200 g |
| polyvinylpyrrolidone | 50 g |

500 g of sarprogrelate hydrochloride, 250 g of lactose monohydrate, 200 g of microcristalline cellulose and 50 g of polyvinylpyrrolidone are dry mixed, granulated with ethanol in a high shear granulator DIOSNA® and, finally, dried under vacuum at 40° C.

Step 2: Compression

| | |
|---|---|
| Step 1 granules | 500 g |
| compressible sugar | 275 g |
| crospovidone | 24 g |
| artificial beef aroma | 200 g |
| magnesium stearate | 1 g |

500 g of the granules obtained in step 1 are mixed with 200 g of artificial beef aroma, 275 g of compressible sugar, 24 g of crospovidone and 1 g of magnesium stearate are compressed, with a FROGERAIS® press, in oblong, two-parts breakable compounds of 200 mg each.

Example 7: Contribution of Serotonergic System in Drug-Induced Valvulopathy to Valvular Heart Disease Thirty-eight degenerated human valves were collected during cardiac valve replacement, in the Department of Cardiovascular surgery (University Hospitals of Strasbourg). 21 aortic and 17 mitral degenerated valves were analyzed by RT-qPCR. Normal mitral and aortic valves were obtained from an explanted heart (a 55 year-old male) at the time of transplantation for a heart failure of non-valve origin and served as controls. The disease etiologies of collected cardiac valve tissues were distributed as following: 12 aortic stenosis, 5 aortic regurgitations, 4 bicuspid aortic valves, 12 mitral valve prolapses, 2 Barlow's disease and 3 rheumatic heart diseases. The results are the following:

1) the $5\text{-HT}_{2A}$ and $5\text{-HT}_{2B}$ receptors (5-hydroxytryptamine receptors 2A and 2B: $\text{HTR}_{2A}$ and $\text{HTR}_{2B}$) mRNAs are detected in all human aortic and mitral pathologic cardiac valves in similar amounts.

2) The expression of $\text{HTR}_{2B}$ mRNA in pathological valve tissues compared to healthy ones is 5-10 fold higher, while $\text{HTR}_{2A}$ mRNA is not significantly different from the control (Table 11): Quantification of $5\text{-HT}_{2A}$ and $5\text{-HT}_{2B}$ receptors mRNAs was performed by real-time quantitative PCR from mitral degenerative (MV) (n=17) and aortic valves (AV) (n=21), compared to normal mitral and aortic valves (n=1). Results are normalized to 18S and presented relative to normal MV or AV. Data are expressed in fold control as mean $2^{-\Delta\Delta Ct}\pm$SD.

TABLE 11

Serotonin receptors ($5\text{-HT}_{2A}$ and $5\text{-HT}_{2B}$ receptors) expression in cardiac valves

| Expression of $5\text{-HT}_2$ receptors | Aortic valves | Mitral Valves |
|---|---|---|
| $2^{-\Delta\Delta Ct}$ ($\text{HTR}_{2B}$-18S) | 4.9 [1.83; 13.16] | 10.14 [5.78; 17.77] |
| $2^{-\Delta\Delta Ct}$ ($\text{HTR}_{2A}$-18S) | 0.72 [0.20; 2.62] | 0.77 [0.41; 1.44] |

3) The $\text{HTR}_{2B}$ over-expression is observed whatever the etiology (Table 12):

Table 12: Comparison of Serotonin Receptors ($5\text{-HT}_{2A/2B}$) mRNA Expression Based on Etiology of Valvular Lesions: Analysis by RT-qPCR.

Values are means±SD, *p<0.05 statistical significance (unpaired t-test between $\Delta$CT ($\text{HTR}_{2A}$-18S) versus $\Delta$CT ($\text{HTR}_{2B}$-18S) for each etiology, n=number per group.

| Etiology of valvular lesions | $\Delta$CT (HTR2A-18S) | $\Delta$CT (HTR2B-18S) |
|---|---|---|
| Aortic stenosis (n = 12) | 16.39 +/− 1.88 | 12.32 +/− 1.25* |
| Annuloaortic ectasia (n = 5) | 16.00 +/− 1.46 | 12.36 +/− 1.42* |
| Bicuspid valve (n = 4) | 14.75 +/− 3.13 | 12.06 +/− 0.87 |
| Mitral valve prolapse (n = 12) | 15.96 +/− 1.08 | 12.41 +/− 0.77* |
| Rheumatic heart disease (n = 3) | 16.27 +/− 0.28 | 13.19 +/− 0.35 |
| Barlow's disease (n = 2) | 15.97 +/− 0.5 | 11.42 +/− 0.11 |

Then, the expression of $5\text{-HT}_2$ receptors in 5 aortic and 5 mitral degenerated valves were analyzed by Western blots. The results are the following:

Compared to control, a 3 fold increase of the $5\text{-HT}_{2A}$ receptor protein in mitral valves (2.98±0.69) and a 6 fold increase in aortic pathologic tissue (6.37±1.97) were observed. For the $5\text{-HT}_{2B}$ receptor protein, a 11 fold increase in mitral valves (10.99±5.11) and a 2.6 fold in aortic samples (2.63±0.99) were found.

Moreover, $5\text{-HT}_{2B}$ receptor expression is found, by immunohistochemistery, in endothelial cells (at the valve surface) but also inside valve lesions. The percentage of $5\text{-HT}_{2B}$ positive cells is 40.2±4.2% in mitral valve lesions (n=4 mitral valve prolapse) and 35.5±3.9% in aortic valve lesions (n=4 aortic stenosis), compared to total cells per 0.03 mm$^2$.

To summarize, $5\text{HT}_{2A,2B}$ receptors are expressed in aortic and mitral human degenerative valves. These two $5\text{-HT}_2$ receptors contribute to cardiac valve degeneration and could be therapeutic targets.

Example 8: (Human) Oral Compound (50% of Sarpogrelate Hydrochloride)

Compounds comprising sarpogrelate hydrochloride are prepared according to a two-steps process:

Step 1: Granulation

| | |
|---|---|
| sarpogrelate hydrochloride | 500 g |
| lactose monohydrate | 250 g |
| microcristalline cellulose | 200 g |
| polyvinylpyrrolidone | 50 g |

500 g of sarpogrelate hydrochloride, 250 g of lactose monohydrate, 200 g of microcristalline cellulose and 50 g of polyvinylpyrrolidone are dry mixed, granulated with ethanol in a high shear granulator DIOSNA® and, finally, dried under vacuum at 40° C.

Step 2: Compression

| | |
|---|---|
| Step 1 granules | 500 g |
| compressible sugar | 475 g |
| crospovidone | 24 g |
| magnesium stearate | 1 g |

500 g of the granules obtained in step 1 are mixed with 200 g of artificial beef aroma, 275 g of compressible sugar, 24 g of crospovidone and 1 g of magnesium stearate are compressed, with a FROGERAIS® press, in oblong, two-parts breakable compounds of 200 mg each.

The invention claimed is:

1. A method for treating valvular heart disease in a mammal, comprising administering to the mammal in need thereof a pharmaceutical or veterinary composition comprising at least one pharmaceutically acceptable or veterinary acceptable excipient and a therapeutically effective amount of sarpogrelate of the formula:

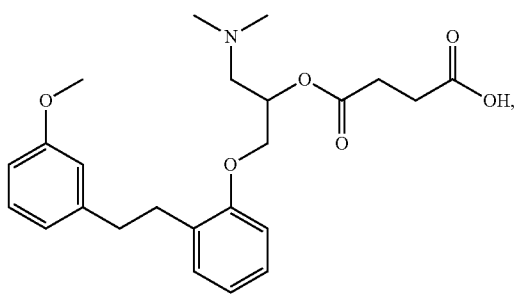 [SMILES: COc1cccc(CCc2ccccc2OCC(CN(C)C)OC(=O)CCC(=O)O)c1]

or the hydrochloride salt thereof.

2. The method according to claim 1, wherein the pharmaceutical or veterinary composition comprises a therapeutically effective amount of sarpogrelate in the range of 0.5 mg to 200 mg.

3. The method according to claim 1, wherein the pharmaceutical or veterinary composition comprises a therapeutically effective amount of the sarpogrelate hydrochloride salt.

4. The method according to claim 1, wherein the pharmaceutical or veterinary composition is administered orally or parenterally.

5. The method according to claim 1, wherein the pharmaceutical or veterinary composition is administered in the range of one time daily to three times daily.

6. The method according to claim 1, wherein the pharmaceutical or veterinary composition is administered after meals.

7. The method according to claim 1, wherein the mammal is a human or a pet.

8. The method according to claim 1, wherein the pharmaceutical or veterinary composition further comprises a buffer agent, a preservative, an oxidant, a diluent, a solubilization agent, a lubricant, or a solvent, or a combination thereof.

9. The method according to claim 1, wherein the pharmaceutical or veterinary composition further comprises one or more additional active ingredients selected from the group consisting of a phosphodiesterase inhibitor, an arterial vasodilator, a platelet aggregation inhibitor, an anorexigen, and an anti-migraine drug.

10. The method according to claim 1, wherein the pharmaceutical or veterinary composition further comprises one or more additional active ingredients selected from the group consisting of cilostazol and pimobendane.

11. The method according to claim 1, wherein the valvular heart disease is characterized by increased valvular mitral thickness and increased cellularity.

12. The method according to claim 1, wherein the valvular heart disease is associated with a pulmonary hypertension.

13. The method according to claim 1, wherein the valvular heart disease results from a carcinoid heart disease.

14. The method according to claim 1, wherein the valvular heart disease results from an initial cardiac valve abnormality.

* * * * *